United States Patent [19]
Shalon et al.

[11] Patent Number: 5,169,522
[45] Date of Patent: Dec. 8, 1992

[54] COLUMN SLURRY PACKING COMPRESSOR

[75] Inventors: Yehuda Shalon; Tadmor Shalon, both of St. Louis, Mo.

[73] Assignee: HT Chemicals, Inc., St. Louis, Mo.

[21] Appl. No.: 587,848

[22] Filed: Sep. 25, 1990

[51] Int. Cl.⁵ ............................................. B01D 15/08
[52] U.S. Cl. ............................. 210/198.2; 210/241; 210/541; 210/656; 55/386
[58] Field of Search .................... 210/241, 198.2, 232, 210/238, 541, 656; 55/67, 386; 141/12, 73, 80

[56] References Cited

U.S. PATENT DOCUMENTS

| | | | |
|---|---|---|---|
| Re. 31,974 | 8/1985 | Brownlee | 210/198.2 |
| 3,440,864 | 4/1969 | Blume | 210/656 |
| 3,453,811 | 7/1969 | Crowley | 55/386 |
| 3,487,938 | 1/1970 | Patterson | 210/198.2 |
| 3,682,315 | 8/1972 | Haller | 210/233 |
| 3,763,879 | 10/1973 | Jaworek | 137/268 |
| 3,771,659 | 11/1973 | Fraser | 210/198.2 |
| 3,855,130 | 12/1974 | Randau et al. | 210/198.2 |
| 3,862,038 | 1/1975 | Takeuchi et al. | 210/198.2 |
| 3,885,800 | 5/1975 | Sievenpiper | 277/165 |
| 3,904,527 | 9/1975 | Wilhelmson | 210/198.2 |
| 3,966,609 | 6/1976 | Godbille et al. | 210/198.2 |
| 4,000,070 | 12/1976 | Sumikama | 210/137 |
| 4,027,816 | 6/1977 | Slator | 277/205 |
| 4,070,285 | 1/1978 | Abrahams | 210/198.2 |
| 4,084,718 | 4/1978 | Wadsworth | 215/247 |
| 4,093,550 | 6/1978 | Stahl et al. | 210/198.2 |
| 4,135,742 | 1/1979 | Anderson | 285/165 |
| 4,162,977 | 7/1979 | Guillemin et al. | 210/198.2 |
| 4,181,853 | 1/1980 | Abu-Shumays et al. | 250/304 |
| 4,280,905 | 7/1981 | Gunkel et al. | 210/198.2 |
| 4,354,932 | 10/1982 | McNeil | 210/198.2 |
| 4,387,075 | 6/1983 | Morgart | 422/50 |
| 4,399,032 | 8/1983 | Mott | 210/198.2 |
| 4,451,364 | 5/1984 | Higgins et al. | 210/198.2 |
| 4,451,365 | 5/1984 | Sattler et al. | 210/198.2 |
| 4,476,017 | 10/1984 | Scharff et al. | 210/94 |
| 4,478,715 | 10/1984 | Walters | 210/198.2 |
| 4,478,720 | 10/1984 | Perrut | 210/659 |
| 4,483,773 | 11/1984 | Yang | 210/656 |
| 4,522,715 | 10/1984 | Goodnight, Jr. | 210/198.2 |
| 4,545,904 | 10/1985 | Tehrani et al. | 210/198.2 |
| 4,549,584 | 10/1985 | Morin et al. | 141/73 |
| 4,557,830 | 12/1985 | Onitsuka | 210/286 |
| 4,563,275 | 1/1986 | McEachern | 210/198.2 |
| 4,578,193 | 3/1986 | Shepherd | 210/656 |
| 4,582,608 | 4/1986 | Ritacco | 210/656 |
| 4,597,866 | 7/1986 | Couillard | 210/198.2 |
| 4,627,918 | 12/1986 | Saxena | 210/656 |
| 4,636,315 | 1/1987 | Allen, Jr. | 210/656 |
| 4,675,104 | 6/1987 | Rai | 210/198.2 |
| 4,692,243 | 9/1987 | Porsch et al. | 210/198.2 |
| 4,732,672 | 3/1988 | Kiang et al. | 210/198.2 |
| 4,732,687 | 3/1988 | Muller et al. | 210/656 |
| 4,737,284 | 4/1988 | Hauke et al. | 210/198.2 |
| 4,737,292 | 4/1988 | Ritacco et al. | 210/656 |
| 4,758,340 | 7/1988 | Marchand et al. | 210/198.2 |
| 4,806,238 | 2/1989 | Sattler et al. | 210/198.2 |
| 4,861,473 | 8/1989 | Shackelford et al. | 210/198.2 |
| 4,874,520 | 10/1989 | Lee | 210/635 |
| 4,876,005 | 10/1989 | America | 210/198.2 |
| 4,882,047 | 11/1989 | Shalon | 210/198.2 |
| 4,888,112 | 12/1989 | Kronwald | 210/198.2 |
| 4,891,133 | 1/1990 | Colvin | 210/198.2 |
| 4,894,152 | 1/1990 | Colvin, Jr. et al. | 210/198.2 |

OTHER PUBLICATIONS

Amicon Advertising Brochure Publication #834, 1987, pp. 1–6.

*Primary Examiner*—Ernest G. Therkorn
*Attorney, Agent, or Firm*—Sandler, Greenblum, & Bernstein

[57] ABSTRACT

A liquid chromatography column that can be rapidly packed without a reservoir column is disclosed. The column includes a double sealed compressor piston with a mixture delivery bore extending through the body of the piston. Resilient sealing means are provided in annular grooves provided in the piston. The piston retains a frit and slurry scraper is mounted to the piston. A method of packing such a column is also disclosed. An outlet end plate including solvent drainage bores is provided. A threaded end cap including radial slots in an inner surface for a threaded column is disclosed, as is an adaptor for joining flanged and threaded columns.

12 Claims, 4 Drawing Sheets

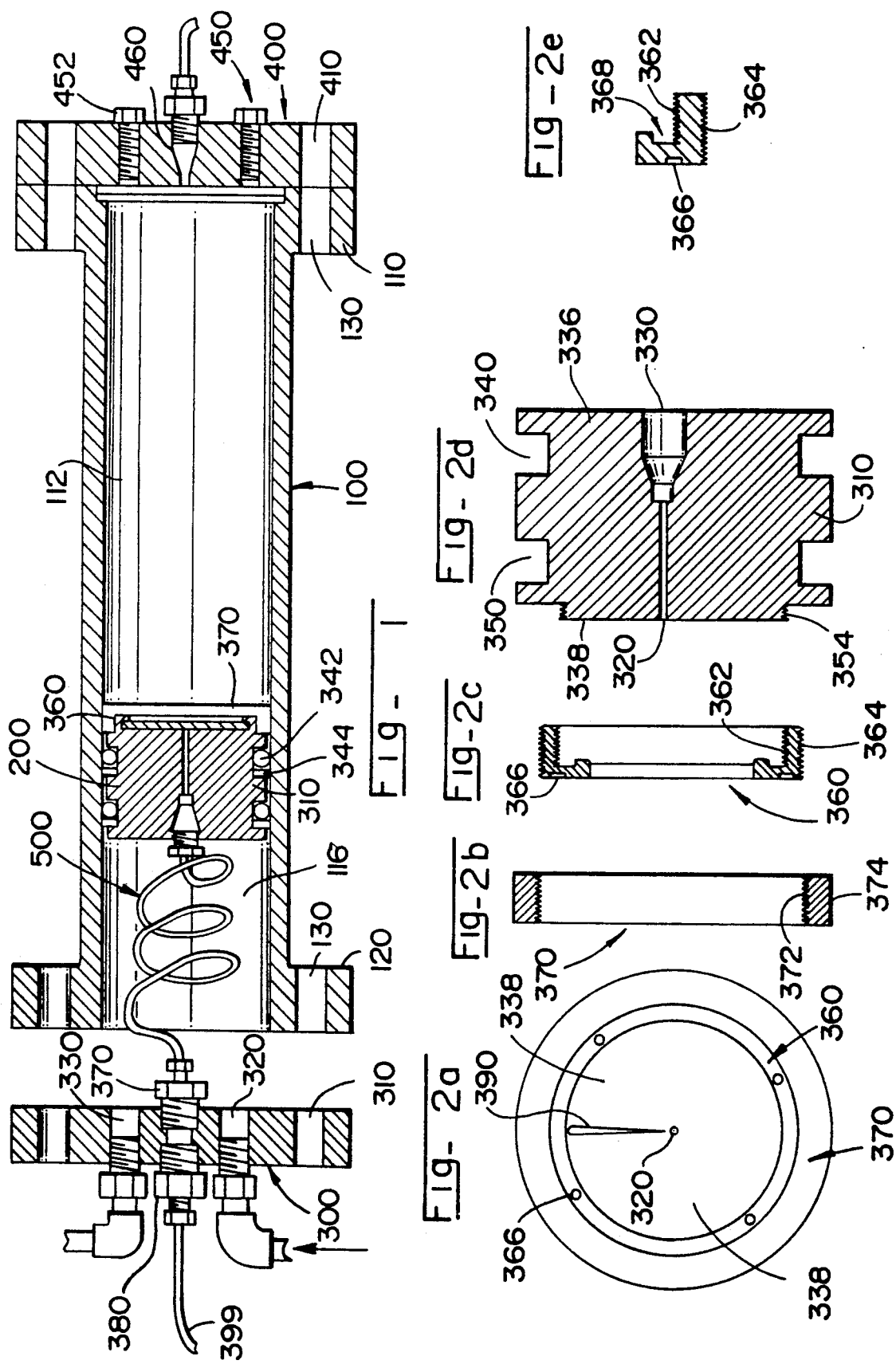

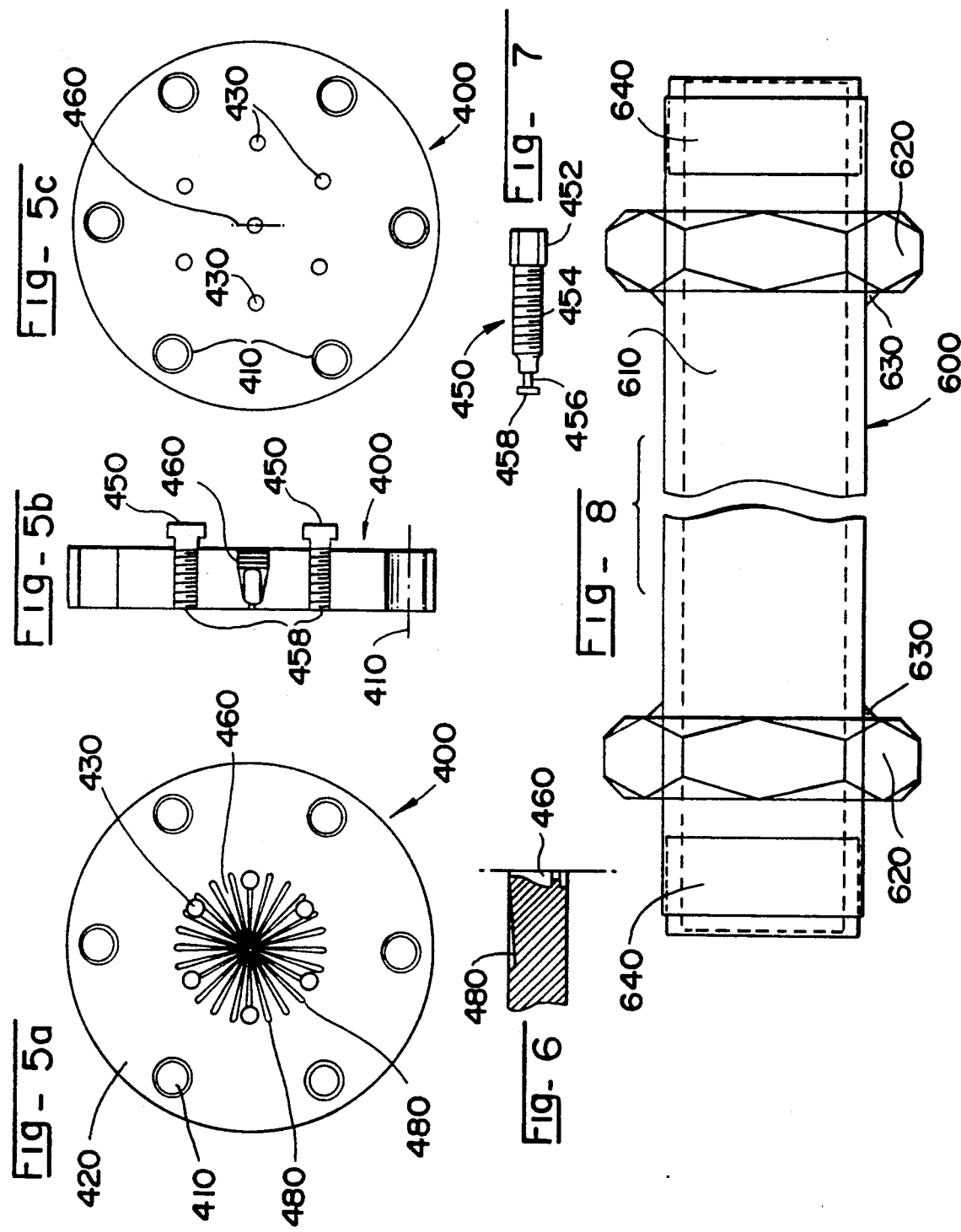

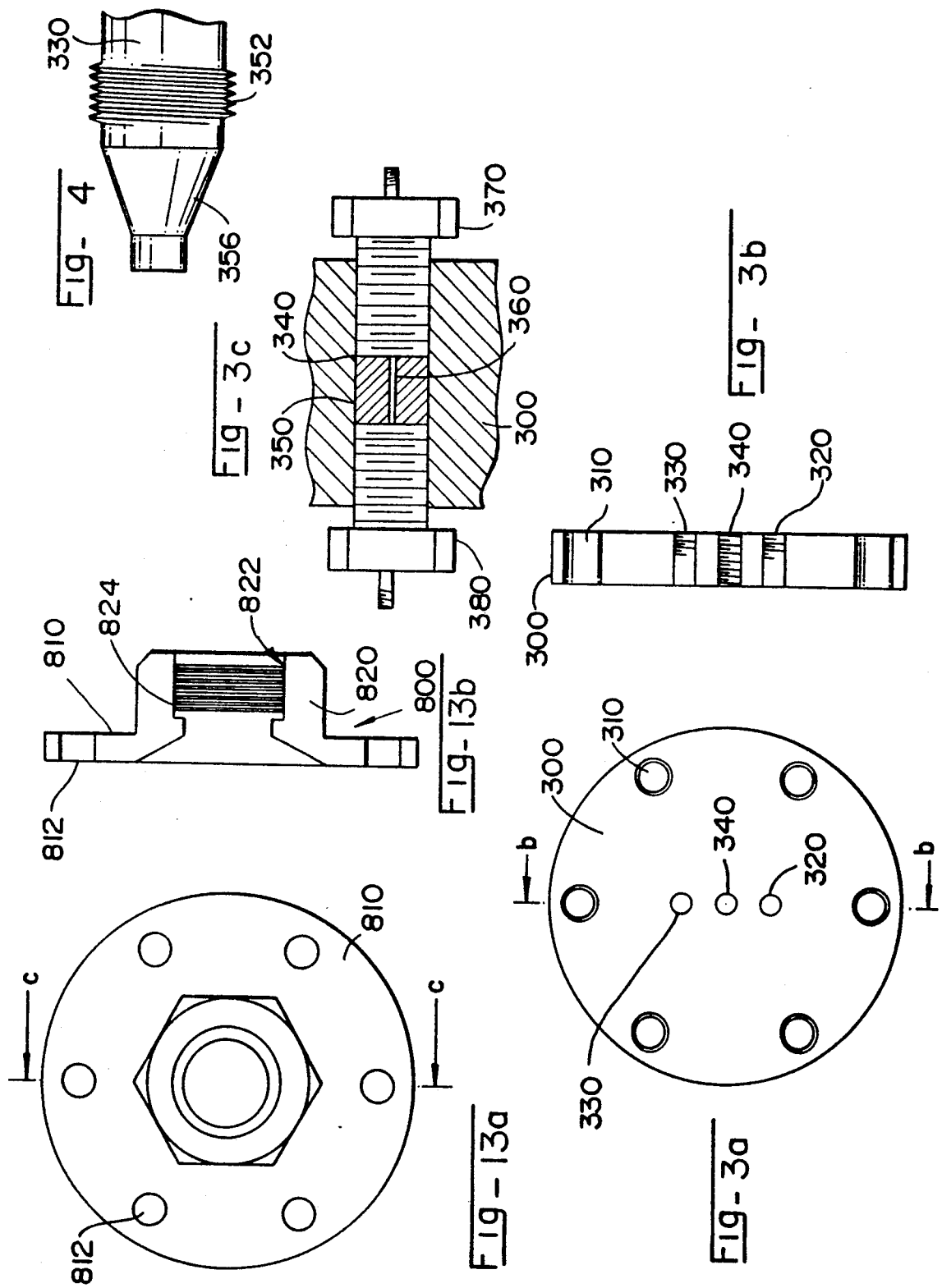

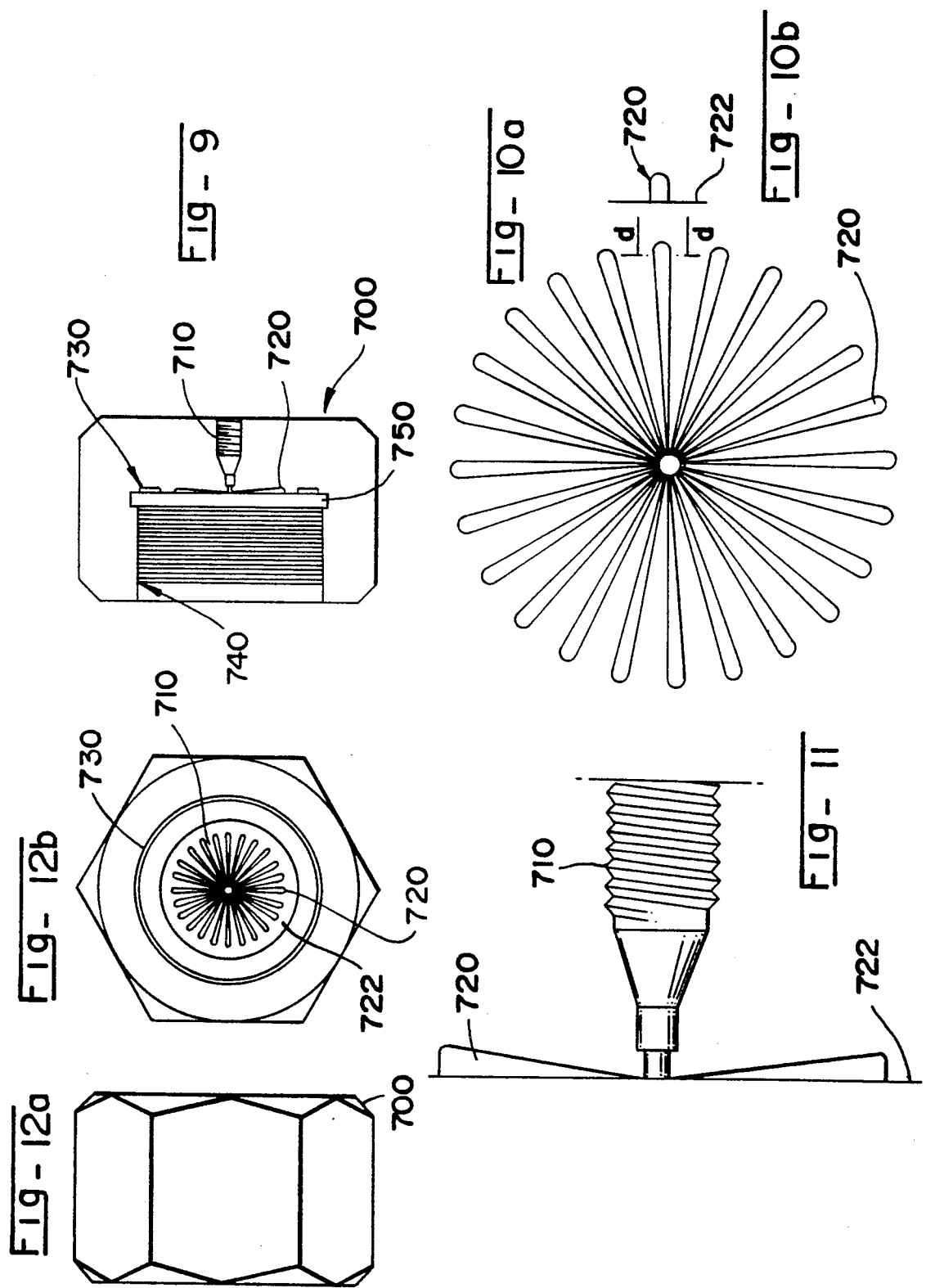

COLUMN SLURRY PACKING COMPRESSOR

BACKGROUND OF THE INVENTION

1. Technical Field of the Invention

The present invention relates to the field of liquid chromatography. In particular, the present invention is directed to an improved apparatus for use in obtaining packed and pressurized slurry beds employed in liquid chromatography columns, as well as novel and improved piston compressors and end closure members for use in such liquid chromatography columns. The present invention is also directed to a method for packing liquid chromatography columns.

2. Description of Background Information

Chromatography is a separation method wherein individual chemical compounds which were originally present in a mixture are resolved (i.e., separated) from each other by the selective process of distribution between heterogeneous phases. The distribution of chemical species to be separated occurs in a dynamic process between a mobile phase and a stationary phase. The stationary phase, or the column packing material, usually has a relatively large surface area through which the mobile phase is allowed to flow. The chemical nature of the stationary phase exercises the primary control over the separation process. The greater the affinity of a particular chemical compound for the stationary phase, the longer it will be maintained in the system. The mobile phase can be either gas or liquid; correspondingly, the methods of chromatography are referred to as liquid and gas chromatography.

Chromatography has been used primarily as a separation and isolation method, and is often utilized to separate many component mixtures in a single step procedure Chromatographic methods can be applied to a very wide concentration range; from commercial scale quantities (gram—kilogram range) all the way to analytical determinations on the order of $10^{-9}$ gram. Chromatographic separations are based upon the physicochemical principles of absorption and partition, and, conversely, these and related fundamental physicochemical phenomenon can be studied by high precision chromatography of model systems.

In liquid chromatography, the mobile phase may be percolated through the column at atmospheric pressure, by means of gravity, or, under more contemporary procedures, through the pressure generated by a suitable pump upon smaller and smaller particles of the packed media. High pressure pumps which can generate up to several thousand psi (pounds per square inch) of inlet pressure are often used.

Thus, high pressure liquid chromatography is a process of separating complex mixtures of chemicals by passing a solution of the chemicals through a stationary column packing material under a certain degree of pressure. Preparative high pressure liquid chromatography is a process in which one applies a mixture of a compound in solution and in its mobile phase wherein, by virtue of the selection of the components of the column packing material, the column will retain the varied and selected components of the mixture for that length of time which causes its select components to be eluted discretely for separate collection as individual components and as purified elements. In preparative high pressure liquid chromatography the separation and purification is in large quantities than in analytical high pressure liquid chromatography.

Increasingly, preparative liquid chromatographic separations are being carried out using porous, silica based, or polymeric microparticular column packings. These materials offer the advantages of increased resolution and improved overall performance in chromatographic separations.

The field of liquid chromatography has long been utilized within the fields of chemistry, biochemistry, and biotechnology. Generally speaking, in practicing the art of chromatography, a slurry is packed within a preparation column under pressure. In order for the chromatographic separation process to be effective, the slurry bed within the column must be compacted to a uniform degree. Further, such uniform compaction must be done rapidly and at moderate cost in order to enable use of chromatographic processes in commercial material production. It has been an ongoing problem in this field to achieve rapid, unfailing and uniform packing of columns. The present invention provides a novel solution to this and other problems in the field of liquid chromatography.

Recently, the field of liquid chromatography has grown to include what is known as high pressure liquid chromatography (HPLC), wherein the columns to be packed are employed as analytical semi-preparative or process columns for use in chromatography. The columns used in chromatographic analysis are generally fabricated of metal, such as stainless steel, and function to separate various chemicals (for analysis or for use) that pass through the columns at pressures that range from 2000 to 4000 psi. By the use of a liquid chromatography column, the chemicals passed through the absorbent bed are separated into their constituents so that the various desired elements can be obtained, or an analysis of the chemicals passing through the column can be performed.

A critical feature in ensuring the proper operation of such columns relates to the degree and uniformity of compactness of the packed absorbent bed contained within the column. The slurry bed must be maintained at very high pressure, and at uniform density, in order to achieve the most efficient end results during the chromatographic procedure. The present invention relates to the configuration and structure of columns for use in preparative liquid chromatography. The present invention also relates to an apparatus for ensuring the rapid and uniform packing of slurry beds. The present invention enables such columns to be uniformly packed, while at the same minimizing the time necessary for packing the column. The present invention also relates to a novel piston compressor for use within the chromatography column that is particularly designed to prevent the leakage of particles past the compressor, while at the same time permitting the injection of a material to be separated through the piston into the compressed bed. The piston compressor of the present invention is utilized to apply a packing compression force to the slurry bed within the column during packing of the column, and, during use of the column in the separation process, is retained within the column. By use of the piston compressor of the present invention, the need for a separate reservoir column is eliminated.

The present invention also relates to an end plate for use with a chromatographic column. In particular, the present invention relates to an outlet end plate which is provided with drainage apertures to enable the solvent to drain from the slurry while the slurry is being compressed by the application of fluid pressure to the compressor piston. Drainage plugs are provided for sealing these drainage apertures or openings during the utilization of the packed column in the separation process.

The present invention further relates to a method of packing and using a column including the novel piston compressor and end plate of the present invention. The method of the present invention enables columns to be packed efficiently and in a very short time period. It also enables a large number of columns to be prepared with a single packing apparatus, and avoids the need for a separate reservoir column to pack the chromatography column.

As a further embodiment of the present invention, an improved threaded column is also provided. The threaded column of the present invention is provided with threaded end caps or nuts which contain, on the respective inner surfaces thereof, a material dispersing means. The material dispersing means comprises a plurality of radially extending grooves or slits in the interior surface of each threaded end nut.

The chromatography column of the present invention includes a compressing piston, movable, by the application of solvent pressure exerted thereagainst, within the bed, which is maintained under dynamic compression via the piston, during column operation. Thus, the present invention allows the user to pack any desired stationary phase quickly, and then enables the packing instrument (fluid/solvent pump) to be utilized to pack additional columns quickly and efficiently. According to the present invention, the desired packing material is transferred into the column, via the outlet end, with the piston in its lowest position (i.e., adjacent the inlet end). After the column outlet end plate is attached, the piston is raised (i.e., pushed into the packing material) by hydraulic pressure applied by the packing instrument, to pack (compress) the material. The applied hydraulic pressure is retained between the back face of the piston and the inlet plate of the chromatographic column. Thus, after packing, the compressor piston of the present invention maintains a dynamic pressure on the packed particle bed which is greater than the pressure of the mobile phase flowing through the column. The dynamic action of the piston prevents the formation of any undesirable voids or channeling due to bed shrinkage.

Thus, columns packed according to the present invention provide total control of the packing process. Columns packed according to the present invention are very efficient. High pressures can be utilized in columns packed according to the present invention and very small sized particles can be employed at high flow rates. Thus, very high material throughputs are achievable. The constant piston pressure that is maintained upon the packed bed during use of the column minimizes and/or eliminates the formation of voids and channeling within the column. Further, excellent reduced plate height values are obtained using the column of the present invention. The packing and unpacking of the column is very simple and quite rapid. The present invention thus simplifies the procedure for packing columns, and, because of its simplicity, speed and moderate cost, makes high quality liquid chromatography accessible to a greater class of users.

The high pressure liquid chromatography system of the present invention has been designed and engineered for efficient and rapid purification of complex mixtures particularly in pharmaceutical and biotechnological environments. The design of the column of the present invention has been optimized to ensure long term operation with minimal maintenance. The present invention includes a plurality of features which ensure low dead volume and very uniform sample distribution over the entire cross-section of the column. The present invention is designed for use at pressures of up to 140 bar (approximately 2000 psi).

According to a significant feature of the present invention, the packing instrument (i.e., an air-driven solvent pump) used with the column establishes the initial pressure on the packed slurry bed. The pressure chamber, and thus the column, remains pressurized even after the packing instrument is disconnected from the column. Thus, the solvent delivery system (instrument) can be reused immediately after disconnection of the packed column therefrom.

The chromatography column of the present invention comprises an inlet plate, a double sealed compressor piston sealingly received within the column body, coiled tubing connecting the inlet end plate with the double sealed compressor piston and an outlet end plate. Appropriate porous frits and sealing O-rings are also provided as part of the column assembly. The inlet end plate is provided with three threaded openings, one of which is equipped with a valve and connector for connection to a pushing solvent delivery system. The valve is closed, upon disconnection of the pushing solvent delivery system, to maintain the pressure within the chromatography column. The central opening in the inlet end plate is connected on one side to the double sealed piston via the tubing, and on the other side to a supply feed line to enable the injection of samples or mixtures into the chromatography column through the inlet end plate, through the coil tubing, the double sealed piston, and finally into the packed bed. The third opening in the inlet end plate is equipped with a liquid gauge and valve to enable monitoring, maintaining, and releasing of the pressure in the chromatography column. The inlet end plate further includes a plurality of apertures or bores for receiving therein bolts which cooperate with appropriate nuts and washers to assist in mounting and sealing the inlet plate, via an appropriate O-ring, to an apertured flange provided on the column body.

The coiled tubing is equipped with tubing connectors at each end. The tubing connectors enable the tubing to be sealingly connected to the piston and to the inlet end plate. As, during packing of the column, the piston is driven by the solvent delivery system down into the column, the tubing must be long enough to extend the length of the column.

The column is a standard chromatography column formed, for example, of stainless steel and having a smooth and accurately ground interior diameter. The column should be large enough to contain enough slurry in its looser, unpacked state so as to yield a packed bed of the required size therein, as well as to contain the compressor piston therein.

The compressor piston is a significant feature of the present invention. The piston includes a generally cylindrical piston body and two annular grooves, formed in the outer, peripheral, cylindrical surface of the piston body and spaced from each other along the length of the piston body and within which O-rings and backup rings are positioned to seal the piston against the interior surface of the column body. The front end face (towards the packed bed) of the piston is provided with a plurality of radially extending slots or grooves to enable and enhance a uniform dispersal of the material to be separated across the entire cross-sectional width of the column. A frit is retained within a frit holder which is attached to the front end face of the piston and a slurry scraper is secured to the outer perimeter of the frit holder.

The outlet end plate utilized in the present invention is provided with a threaded central opening to enable the attachment of a tubing connector so that the separated compounds from the packed bed within the chromatography column can flow out through the tubing attached to the tubing connector. Additionally, a plurality of bolt receiving apertures or holes, generally similar to the bolt holes or apertures provided in the inlet end plate are provided. The outlet end plate is attached to the appropriate end flange of the chromatography column via nuts, bolts and washers, as is conventional. In addition, the outlet end plate is provided with a plurality of radial slots or grooves extending from the central threaded opening towards the periphery of the plate in order to enable the chemicals separated throughout the column to be collected to flow through the outlet end plate. In addition, in another significant feature of the invention, the end plate is provided with a plurality of threaded holes or bores for receiving appropriately sized packing drain plugs. The drain plugs are provided to seal the threaded holes or bores during use of the column for separation; but, during the packing of the column, are removed so that the packing solvent can be ejected from the column.

Operating the chromatography column of the present invention to pack a compressed bed is very easily performed. First, the piston and its components, including the various sealing members, the frit holder and the slurry scraper, are assembled, and the piston is inserted into the column, by use of an adapter member, in a position closely adjacent to the inlet end plate. The central opening of the inlet end plate is then connected via the tubing to the piston. Then, after an appropriate O-ring is installed in the column flange, the inlet end plate is secured to the column body via nuts and bolts extending through the mating apertures in the flange of the column and in the apertures of the inlet end plate. The slurry is loaded into the column on top of the piston until the column is almost full (an air bubble must be left to enable proper mixing). The outlet end plate is then attached by appropriate nuts and bolts and the drainage plugs are removed therefrom. The airpump driven high pressure solvent delivery system attached to one of the threaded openings in the inlet end plate is then actuated to rapidly drive the piston down into the slurry loaded into the column, to compress the slurry and to expel the solvent from the open drain bores. After all the solvent has drained out of the drain bores and the column is allowed to equilibrate for an appropriate period of time, the valve connecting the inlet end plate to the liquid delivery system is closed so that the pressure is retained within the column between the rear face (i.e., the surface facing the inlet end plate) of the piston and the inlet end plate. The drain plugs are then inserted into the drain bores in the outlet end plate, and the packed column can then be disengaged from the high pressure solvent delivery system. After connection of the packed column to a chromatography pump to deliver the mobile phase material, chromatography can be performed.

SUMMARY OF THE INVENTION

The present invention relates to a slurry packing compressor for use in a chromatographic column which is adapted to contain a bed of particles comprising a slurry. The compressor includes a generally cylindrical piston including structure for receiving a resilient means adapted to seal an interface of a chromatography column and the piston. A material to be separated is adapted to be injected into the bed of particles, and a mechanism is provided for dispersing the material to be separated throughout the cross section of the column. The compressor also includes a device for retaining a frit.

The piston of the invention further includes a packed-bed facing end-surface, a pressure-receiving end-surface, and a cylindrical body portion extending between the end-surfaces. The structure for receiving the resilient means comprises a plurality of annular grooves provided in the cylindrical surface of the piston, each groove adapted to receive a resilient sealing means. Further, each resilient sealing means comprises a resilient O-ring and backup spacer member. Further, each backup spacer member comprises a split ring glass loaded polymer. Each resilient O-ring is positioned within each groove to be closer to the packed bed facing end-surface of the piston than the backup spacer member.

According to another feature of the invention, the piston includes a threaded portion adjacent to the packed-bed facing endsurface of the piston, and frit retaining device is adapted to threadedly engage the threaded portion. The frit retaining device is capable of receiving a frit sealing member. The frit retaining device further comprises structure for mating with a tool for tightening and loosening the frit retaining device with respect to the piston.

Further, the frit retaining device further includes a structure for receiving a slurry scraping member. The slurry scraping member comprises an annular member threadably engaging a mating threaded portion of the frit retaining device.

According to another feature of the invention, the material to be separated is injected into the slurry bed via a bore extending through the piston. The bore sealingly mates with a supply line for delivering a material to be separated through the piston into a packed bed retained in the column.

According to another feature of the invention, a mechanism is provided for ensuring the uniform dispersal of a material to be separated throughout the column. The mechanism comprises a plurality of radially extending slots or grooves disposed in the packed bed facing end-surface of the piston.

The present invention also relates to an adaptor member for connecting flanged and threaded liquid chromatography columns. The adaptor comprises a first flanged portion and a second threaded portion integrally connected to the flanged portion. The adaptor member further comprises structure for retaining an O-ring between the first and second portions. Further, the first portion includes a plurality of apertures adapted to receive bolts for securing the adaptor member to a flanged chromatography column, and the second portion includes threads adapted to mate with the end of a threaded chromatography column.

The present invention also relates to a chromatography column assembly including a column comprising inlet and outlet ends, the interior of the column comprising a chamber adapted to retain a packed slurry bed. The column assembly further includes an inlet end plate and an outlet end plate, the end plates including a mechanism for enabling the plates to be sealingly secured to the column. Further, the assembly includes a compressor piston adapted to be positioned within the chromatography column and including structure for ensuring leakproof engagement between the piston and the interior of the column. Structure is connected to the inlet end plate and extends through the compressor piston for delivering a material to be separated into the packed slurry bed. Further, a mechanism is provided for draining the slurry solvent from the chamber through the outlet end plate. The assembly also contains means for retaining a frit adjacent the end of the piston facing towards the packed slurry bed.

The inlet end plate further includes a mechanism for enabling the application of hydraulic pressure to the piston to pack the slurry bed and for maintaining piston pressure during use of the column for separation. The pressure application mechanism comprises disconnectable means for exerting a hydraulic pressure against the compressor piston and a mechanism for retaining the exerted pressure after disconnection of the exerting means.

Further, the outlet end plate comprises a plurality of solvent drainage apertures or bores which comprise the draining mechanism. The compressor piston further includes structure ensuring the uniform dispersal of a material to be separated throughout said column. The compressor piston includes a plurality of radially extending slots or grooves disposed in an end surface of the piston facing towards the packed slurry bed, with the slots comprising the structure for ensuring the uniform dispersal of a material to be separated throughout the column. The structure for ensuring leakproof engagement between the piston and the column includes a plurality of annular grooves provided in a cylindrical surface of the piston, each groove adapted to receive a resilient sealing mechanism. Further, each resilient sealing mechanism includes a resilient O-ring and a backup spacer member.

The present invention also relates to a method of packing a liquid chromatography column having means for securing inlet and outlet end plates to the flanged ends of the column. The method comprises positioning a compressor piston having first and second end faces within the column, connecting a material supply line between an inlet end plate and a second end face of the piston, securing the inlet end plate to the column, and substantially filling the column above the first end face of the piston with a slurry. The method further includes securing an outlet end plate to the column, applying pressure, from a pressure source, to compress the slurry between the first end face of the compressor piston and the outlet end plate, allowing the slurry solvent to drain through the outlet end plate, and sealing the end plate after the solvent has been drained from the compressed slurry.

The method further comprises the step of retaining a frit adjacent a first end face of the piston, and supplying a material to be separated within the compressed slurry through the piston. The pressure between the inlet end plate and the piston second face is retained after disconnection of the column from the source of pressure, and a plurality of annular, resilient, seal-containing formations are provided between the first and second faces of the piston.

The method of the present invention further includes uniformly dispersing a material to be separated throughout the column. Ensuring the uniform dispersal of a material to be separated involves disposing a plurality of radially extending slots (or grooves) within a first end surface of the compressor piston. The present method further includes the provision of a slurry scraping member attached adjacent the first end face of the compressor piston.

The present invention also relates to an outlet end plate for use with a liquid chromatography column containing a bed of particles comprising a slurry. The outlet end plate comprises a first mechanism for enabling the solvent to be drained from the bed of particles to enable the bed of particles to be compressed, a second mechanism for enabling separated materials to be conducted from the compressed slurry bed within the column, and a mechanism for disabling the first mechanism after the slurry bed is compressed.

The first mechanism comprises a plurality of drainage apertures. The disabling mechanism comprises a plurality of drainage plugs adapted to seal the drainage apertures. The second mechanism comprises a central outlet aperture including a plurality of slots or groove extending radially from the central outlet aperture.

A further feature of the present invention relates to a threaded end nut or cap for use with a thread-ended chromatography column. The end nut comprises a cylindrical, threaded portion adapted to be threadably engaged with the end of a liquid chromatography column, and an end portion extending from and transversely to the threaded portion. The end portion comprises an aperture enabling a fluid mixture to pass through the end portion, and further comprises a plurality of slots or grooves extendingly radially from the aperture, the grooves provided in a surface of the end portion adapted to contact a compressed slurry bed within the chromatography column.

The slots or grooves extend radially from the aperture towards the threaded portion and increase in volume in a direction 10 moving away from the aperture. According to a further feature of the invention, the grooves increase in depth in a direction moving away from the aperture. The end nut also comprises means for sealingly receiving a frit, and means for sealingly receiving the end of the chromatography column.

BRIEF DESCRIPTION OF THE DRAWINGS

The invention is further explained in the detailed description which follows, with reference to the drawings, by way of non-limiting examples of the various embodiments of the invention, in which like reference numerals represent similar parts throughout the several views, and wherein:

FIG. 1 is a sectional side view of the flanged chromatography column according to a first embodiment of the present invention with the outlet end plate secured thereto, and the inlet end plate separated therefrom;

FIG. 2A–2E are various views of parts of the compressor piston of the present invention, Wherein:

FIG. 2(a) is an end view of a first inner packed-bed contacting end face of the piston;

FIG. 2(b) is a sectional side view of the scraper of the compressor piston of the present invention;

FIG. 2(c) is a sectional side view of the frit holder of the present invention;

FIG. 2(d) is a sectional side view of the body of the compressor piston of the present invention;

FIG. 2(e) is an enlarged sectional side view of a portion of the frit holder shown in FIG. 2(c);

FIG. 3(a) is an end view of an inlet end plate of the present invention;

FIG. 3(b) is a cross sectional view of the inlet end plate of FIG. 3(a) taken along the line b-b thereof;

FIG. 3(c) is an enlarged cross sectional view of the center aperture of the inlet end plate of FIG. 3(b) with inner and outer tubing connectors attached thereto;

FIG. 4 is a side view, on a greatly enlarged scale, of a center aperture of the general type provided in the inlet and outlet end plates, as well as in the piston, showing the shape and threading thereof adapted to threadably receive a tubing connector;

FIG. 5(a) is an end view of the interior facing surface of the outlet end plate of the present invention;

FIG. 5(b) is a cross sectional side view of the outlet end plate of the present invention, showing the packing drain plugs inserted therein;

FIG. 5(c) is an end view of the exterior facing surface of the outlet end plate of the present invention;

FIG. 6 is a sectional side view, on a greatly enlarged scale, of a portion of the outlet end plate of the present invention showing a radially extending slot or groove formed therein;

FIG. 7 is a side view of an outlet end plate packing drainage plug;

FIG. 8 is a side view of a thread ended chromatography column according to another embodiment of the present invention;

FIG. 9 is a cross sectional side view of the threaded end cap or nut of the embodiment of the invention shown in FIG. 8;

FIG. 10(a) shows on an enlarged scale, the distribution and shape of the radial slots or grooves disposed in the interior end surface of the threaded end nut or cap of FIG. 9;

FIG. 10(b) represents the cross sectional shape of one end of the radial grooves taken along line d - d of FIG. 10(a);

FIG. 11 shows, in a greatly enlarged scale, the shape of the threaded aperture provided in the end face of the threaded nut, as well as a representative cross-sectional view showing the increasing depth of the radial grooves provided in the interior end face of the threaded nut of FIG. 9;

FIG. 12(a) is an exterior side view of the threaded nut of FIG. 9;

FIG. 12(b) is an end view of the nut of FIG. 9, showing the arrangement of radial grooves provided in the interior surface thereof, as well as the O-ring retaining groove positioned therein;

FIG. 13(a) is an end view of the threaded and flanged adaptor/connector member according to a feature of the invention; and FIG. 13(b) is a side sectional view taken along line c—c of FIG. 13(a) of the threaded and flanged adaptor/connector member.

DESCRIPTION OF THE PREFERRED EMBODIMENT OF THE INVENTION

With reference to the drawings and in particular with reference to FIG. 1, there is illustrated, in sectional side view, a self slurry packing column according to a preferred embodiment of the present invention. The column includes a column body 100, having an inlet flange 120 and an outlet flange 110 rigidly secured thereto. Each of the inlet and outlet flanges is provided with a plurality of apertures 130 disposed about the periphery thereof, by means of which corresponding inlet and outlet end plates 300 and 400 can be secured to the column body 100. The column body 100 is formed of stainless steel or other suitable chemically resistant material and the inner diameter of the column body is smoothly finished so as to be able to sealingly receive therein the compressor piston 200 of the present invention. The column body 100 can be formed with any desired diameter and should be of a length large enough to contain the piston as well as to contain enough slurry material to form a packed bed of the desired length.

With reference to FIGS. 1 and 3(a), (b) and (c), an inlet end plate 300 is illustrated. The inlet end plate 300 is provided with a plurality of apertures 310 provided about the periphery thereof. The apertures 310 are spaced so as to mate with the apertures 130 in the inlet end flange of the column when the inlet end plate is positioned over the inlet end flange of the column. Appropriate hardware (nuts, bolts and washers) is utilized to securely retain the inlet end plate on the column body and an O-ring is utilized to seal the end plate to the body.

As can most clearly be seen in FIGS. 3(a) and 3(b), the inlet end plate 300 is additionally provided with three threaded openings, 320, 330, and 340, extending therethrough. Threaded opening 320 can have a tubing connector attached thereto, for connection, via a quick connector, to a liquid solvent delivery system which comprises the slurry packing mechanism of the present invention.

Threaded opening 330 is provided, via a quick-connect coupling, with a liquid pressure gauge and a valve, both rated for appropriate pressure (6500 psi/450 bar). The liquid pressure gauge connected through the threaded opening 330 is utilized to monitor, maintain and release the pressure in the chromatography column of the present invention. This valve enables air to be purged from the system so as not to compress air within the system when the slurry bed is compressed by the solvent delivery system, and thus assures the safety of the chromatography packing system of the present invention.

Central opening 340 of the inlet end plate 300, as most clearly illustrated in FIG. 3(c) and is equipped with two tubing connectors 380, 370 mounted to extend in opposite directions. A teflon plug 350 is disposed between the tubing connectors and is provided with a small diameter hole 360 bored through the center of the plug 350 to enable a mixture to be separated to pass through the inlet end plate of the system, and enables the delivery of such mixtures through the inlet end plate into the packed bed contained within the chromatography column for analysis and separation. Thus, the outer tubing connector 380 is connected to an appropriate supply of a chemical mixture to be separated, while the inner tubing connector 370 is connected to the compressor piston which forms a further feature of the present invention.

Connected to the inwardly extending end of the tubing connector 370 is a length of coiled tubing 500 which extends from the tubing connector 370 to a generally similar tubing connector 332 threadably engaged to the piston 200. The coiled tubing, which can be made of stainless steel or any other similar chemically resistant material, connects the piston at one end and the inlet end plate at the other, and enables a material mixture or sample to be fed to and through the compressor piston body. For reasons that will become clear later, the length of the tubing must be long enough to extend substantially over the entire length of the column body.

The piston compressor 200, which forms a significant feature of the present invention, is a double-sealed, slurry packing piston made of assembled components shown in FIG. 1 in their assembled conditions, and in greater detail in FIGS. 2(a), 2(b), 2(c), 2(d) and 2(e). The compressor piston 200 of the present invention can typically be formed of stainless steel or a similar chemically resistant material, and comprises a piston body 310 as shown most clearly in FIG. 2(d). The piston body is of generally cylindrical shape, having a first end face 336, which, when installed in the column, faces the inlet end plate 300. The piston body 310 also includes a second end face 338 that faces the compressed bed of slurry material. Intermediate the end faces 336 and 338, spaced first and second annular grooves 340 and 350 are provided in the cylindrical surface of the piston body 310. Adjacent the end face 338 a necked down portion containing threads 354 is provided. At the center of the end face 336, a threaded aperture for a tubing connector is provided. Into this threaded aperture, a tubing connector 332, which is connected to the coiled tubing 500, is engaged. The threaded opening 330 continues through the piston body as a relatively small bore 320, through which the mixture to be separated passes to reach the frit retained adjacent the end face 338.

Within each of the two wide annular grooves 340, 350, an O-ring 342 and a backup spacer member in the form of a flat, split ring 344 are positioned. The O-ring 342 is formed of a Fluorez (or any other chemically resistant) material, while the split ring 344 is typically formed of glass loaded TFE or a similar polymeric material. Within each groove 340, 350, the O-ring 342 is mounted closer to the slurry contacting end face 338 of the piston compressor 200, while the split ring 344 is mounted closer to the pressure receiving end face 336.

The frit holder 360, shown in a cross sectional side view in FIG. 2(c), is mounted to the piston body 310. The frit holder 360 is provided with a first interior threaded portion 362 which is designed to matingly engage with the threads 354 on the necked down portion of the piston body 310. A second externally threaded portion 364 is provided about the outer surface of the frit holder. As shown most clearly in the enlarged view of FIG. 2(e), the frit holder 360 is shaped such that an O-ring groove 368 is provided therein. A conventional TFE O-ring can be inserted into the groove 368 to seal the frit holder 360 against the piston body 310. The frit holder can be manufactured from stainless steel and should be silver plated to avoid galling or the premature wearing away of the threads 362 thereon by friction between the threads 362 and the mating threads 354, provided on the piston body 310 and which can both typically be formed of stainless steel.

On an outwardly extending end face of the frit holder 360, a plurality, typically four or more, recesses 366 are formed. An appropriately designed and constructed spanner wrench or other pronged tool is provided, having pins which are positioned to mate with the recesses 366 to enable sufficient torque to be applied to the frit holder 360 to enable the frit holder to be tightly mounted on and demounted from the face 338 of the piston 310. By properly tightening down the frit holder against the piston surface, the frit will be tightly retained thereagainst, and, because of the O-ring positioned within the space 368, no packing media will be able to penetrate into the feed line 320.

The frit (non-illustrated) for the piston is designed and sized to fit (i.e., thickness and perimeter) between the frit holder 360 and the face 338 of the piston. The frit holder is manufactured of a porous stainless steel or other porous material as is conventional in the chromatography technology. The porosity of the frit should match (i.e., be smaller than) the particle size of the packing media.

On the outer circumference of the frit holder 360, a threaded portion 364 is provided for enabling the slurry scraper 370 to be retained on the frit holder 360. As is most clearly illustrated in FIG. 2(b), the scraper 370 is generally ring shaped, and is provided with interiorly disposed threads 372 which are designed to mate with the exteriorly provided threads 364 on the frit holder 360.

The scraper 370, formed of TFE or a similar polymer, is provided to prevent the typically stainless steel piston body 310 from possibly scraping and thus damaging the machined stainless steel interior surface of the column body 100. The scraper a)so serves to move the packing media ahead of the piston, and to keep it there so that it does minimum damage to the sealing O-rings on the piston. Further, the scraper prevents grinding and crushing of the packing media between the stainless steel piston and the stainless steel column body.

As shown in FIG. 2(a), the end face 338 of the piston body 310 is provided with a plurality of radially extending slots or grooves. One groove 390 is shown in FIG. 2(a); however, typically 24 or more such grooves are provided in an arrangement similar to that shown in FIG. 10(a) and extending from the central aperture 320 of the piston radially outwardly therefrom to a position adjacent to the peripheral end of the face 338. These radial slots or grooves 390 serve to uniformly disperse the incoming mixture to be separated throughout the cross sectional area of the column. The mixture to be separated is injected via an appropriate supply mechanism, through the supply line 399 extending through the central aperture 340 of the inlet end plate 300, through the tubing 500, through the bore 320 in the compressor piston, through the radial grooves 390, and finally through the frit into the packed slurry bed. The grooves, radially disposed within the end face 338, increase in width and depth as they radiate outwardly from the center of the end face 338, forming a dispersion chamber integrally structured within the end face of the piston to facilitate prompt and uniform distribution of incoming chemicals.

FIG. 4 shows, in a greatly enlarged detail, the shape and structure of the threaded opening 330 provided in the end plate 336 of the compressor piston body 310. Generally similar threaded openings are provided in both the inlet end plate 300 and the outlet end plate 400. As shown in FIG. 4, the threaded opening 330 is provided with a plurality of threads 352 and a tapered section 356 which culminates in a smaller diameter aperture which leads to the narrow bore 320 extending the length of the piston. The threads 352 are designed to accept an appropriate mating quick connect coupling for enabling the connection of tubing, such as coiled tubing 500 to the piston.

The outlet end plate 400 is shown with reference to FIGS. 1, 5(a), 5(b), 5(c), 6 and 7. A centrally positioned threaded opening 460 is provided to enable attachment of an appropriate tubing connector. The tubing connector, attached to this opening, enables the flow of the separated chemicals out of the packed chromatography column. The tubing connector attached to the center aperture or opening 460 is substantially the same as the tubing connectors 370, 380, 332 and is of generally standard and conventional construction.

The outlet end plate is provided, about the periphery thereof, with a plurality of apertures 410 which, in a manner similar to the apertures 310 of the inlet end plate, are positioned and sized to mate with the appropriate apertures in the end flange 110 of the column body. Appropriate nuts, bolts and washers are utilized within the aligned apertures 410, 130 to enable the outlet end plate to be sealingly secured to the outlet end of the column body 100. Disposed interiorly of the outlet end plate 400 are, as is conventional in the chromatography field, a bed support frit, a disperser frit, as well as TFE small and large O-rings. These, and the conventional hardware items discussed above (bolts, nuts and washers), are fully disclosed and set forth in commonly assigned U.S. Pat. No. 4,882,047 (SHALON), the entire disclosure of which is expressly incorporated herein by reference. As disclosed by the above-mentioned patent, the end plate is provided with radial grooves or slots therein to enable the uniform collection of the liquid chemicals from throughout the cross section of the column body and to facilitate their conduction into the outlet flow line via the central aperture 460. The design, structure and sizing of the O-rings, frits, and radial slots or grooves are discussed in the above-mentioned patent.

The outlet end plate 400 is further provided, about the periphery thereof but interiorly of the apertures 410, with a plurality of equally spaced threaded drainage bores 430. These bores 430 are provided for enabling drainage of the slurry solvent during the packing of the column. Received within each one of the bores 430 is a packing drain plug 450, shown most clearly in FIG. 7. Each packing drain plug 450 is shown to have a generally hex shaped head 452 and a straight threaded body portion 454 which mates with the threading provided in the drainage bores 430. Interiorly of the threaded portion 452, an O-ring groove 456 is provided to receive an O-ring therein to seal the drainage bores 430 when the packing drain plugs ar inserted and tightened therein. Each packing drainage plug 450 is sized so that an interiorly disposed flat face 458 is positioned such that when the plug is inserted and tightened within a bore 430 of the outlet end plate 400, the surface 458 will be exactly flush with the inside surface of the end plate to thus avoid creating voids within the packed slurry material.

As can be understood, during the packing of the chromatography column of the present invention, the packing drainage plugs 450 are removed from the bores or apertures 430 so as to enable the slurry packing solvent to drain freely from those apertures as pressure is applied to the slurry material by the piston 310. After the column is tightly packed, these plugs are installed therein and tightened until the surfaces 458 are flush with the interior surface of the outlet end plate 400, so that the separated compounds will flow out through the center opening 460 only.

FIG. 6 shows a cross sectional view of a section of the outlet end plate 400 with the shape of the radially disposed grooves or slots 480 clearly indicated therein.

The flanged end plate chromatography column illustrated in FIGS. 1 through 7 can be packed in a novel manner according to a method of the present invention. First, the piston is assembled. In other words, the flat and circular O-rings 342 and 344 are assembled into each of the annular grooves 340 and 350. A further O-ring is positioned within the O-ring groove 368 that is provided within the frit holder 360. A frit is installed on the face 338 of the piston body, and the frit holder 360 is threadedly mounted thereon. An appropriate tool having pins that mate with the holes 366 is utilized to tightly secure the frit holder and the frit carried thereby onto the piston body. The slurry scraper is then threadedly engaged over the frit holder.

Connector 332 with coiled stainless steel tubing 500 is then inserted into the central threaded aperture 330 of the piston body. The other end of the tubing 500, having a similar threaded connector 370, is inserted into the inwardly facing central aperture of the inlet end plate 300. The piston is then inserted into the body of the column as shown in FIG. 1 by means, for example, of the adaptor member disclosed in co-pending, commonly assigned U.S. Ser. No. 07/501,122 filed on Mar. 29, 1990 in the name of Dr. Y. Shalon, the entire disclosure of which is expressly incorporated herein by reference.

Thereafter, using an O-ring and the appropriate nuts, bolts and washers, the inlet end plate 116 is securely attached to the column flange 120. The region 110 between the rear surface of the piston 336 and the front (i.e., inward) surface of the inlet end plate can then be filled with a pushing solvent at atmospheric pressure, and the apertures 330 and 320 closed by means of the associated valves provided in the couplings threadedly attached to these apertures.

The column should then be mounted in an appropriate stand with the open end (where the outlet end plate will eventually be secured) facing upwardly. Thus, the inlet end plate and piston will be at the bottom of the column. The column interior 112 should then be filled with a slurry, up to within several centimeters of the top. By leaving a space at the top of the column, an air bubble will be formed which will aid in the mixing and the maintenance of a uniform dispersion of packing material within the column. The outlet end plate is then assembled onto the top of the column. The assembling of the outlet end plate onto the upper end of the column involves placing the bed support frit in the frit recess of the column body. The disperser frit and small TFE O-ring are then placed on top of the bed support frit, and the large TFE O-ring is positioned within the flange groove. The outlet end plate is the secured to the outlet flange 110 of the column body 100, with the aid of the nuts, bolts and washers as is conventional and as is disclosed with great particularity in the aforementioned U.S. Pat. No. 4,882,047. After the outlet end plate is securely fastened to the flange 110, the column can be rotated (i.e., inverted) several times to aid in mixing of the slurry. Complete mixing of the slurry should take place within several minutes.

The column should now be inverted within the holder so that the inlet portion of the column is up, and an appropriate solvent pushing instrument should be attached to the aperture 320 via the appropriate quick connector. The solvent delivery system generally uses an air-driven, high pressure pump which is capable of delivering the solvent through the hose fitting and valve into the space 116 provided between the inlet end plate 300 and the end face 336 of the piston. The packing drain plugs 450 have been previously removed from the drainage bores 430 of the outlet end plate, and, as the pump rapidly pushes the piston down at the preset pressure, the solvent within the slurry in the area 112 of the column will be ejected through the drainage bores 430. After several minutes, when no more solvent is observed to be draining out of the drainage bores 430, the packing of the column has been completed and the column should be allowed to equilibrate for several more minutes.

The valve connecting the solvent delivery pump to the inlet end plate aperture 320 can now be closed to retain the fluid pressure within the column portion 116 acting on the piston face 336 to maintain the compressed slurry bed in the volume 112 at the appropriate pressure. The packing drainage plugs 450 should now very quickly be inserted into the bores 430; and after attaching the slurry packing chromatography column of the present invention to the appropriate source of a fluid mixture to be separated, the column can be used.

Because the column is pressurized and the pressure can be maintained within the working column 112 by means of the pressure chamber 116, the column can quickly be removed from the solvent pushing system (i.e., pump), and the pump can be used to pack another column. This makes the packing of a chromatography column incorporating the features of the present invention extremely efficient and quick.

A further embodiment of the invention is disclosed with reference to FIGS. 8 through 12. Chromatography columns are generally either of the flanged type or of the threaded type. FIGS. 1 through 7 relate to a chromatography column of the flanged type. FIGS. 8 through 12 relate to a chromatography column of the threaded type. Chromatography columns having threaded end caps or nuts, as shown in FIGS. 8 through 12, are generally manufactured in a diameter of less than one inch; whereas flanged chromatography columns, as shown in FIGS. 1 through 7, can be made in diameters substantially larger than one inch.

As shown in FIG. 8, the chromatography column 600 comprises a column body 610 having attached, near the ends thereof, hex nuts 620. The hex nuts 620 are each attached to the column 600, as by welding at 630, and facilitate assembly of the end caps to the column by providing gripping surfaces by which the end caps can be tightly installed. Each end of the column 610 is provided with threaded portion 640. End caps or nuts 700 are provided for threadingly engaged the threaded ends 640 of the column 610. As shown in FIG. 9, each threaded end cap 700 includes an internally threaded section 740 designed to mate with the threaded portion 640 of the column 610. Extending through the end portion of the threaded end cap 700 is a threaded aperture 710 which is shown in enlarged form in FIG. 11. Also clearly shown in FIGS. 9, 10 and 11 are the radially disposed slots 720 which increase in both width and depth as they extend away from the central aperture 710. The central aperture 710 is threaded as shown in the enlarged view of FIG. 11 so as to enable connection of appropriately sized tubing connectors to enable a mixture to be supplied to and uniformly dispersed within the column, and also to be collected for output from the column after being separated.

As shown in FIG. 9, the threaded end cap 700 is also provided with two O-ring grooves. The first O-ring groove 730 retains therein a thin, flat O-ring, while the second O-ring groove 750 retains therein an O-ring of substantially circular cross section. Thus, a double seal comprising these two O-rings is utilized to provide an exceptional seal between the end plate and the column, as well as between the end plate and an appropriate frit positioned therein. Because the O-rings, which can typically be formed of a TFE or a similar material, provide a certain amount of resilient give, the threaded end cap column shown in this embodiment of the invention enables the use of frits of various thickness without requiring modification of the column.

FIG. 12(a) shows an exterior view of the hex nut type configuration of the threaded end nut or cap shown in FIG. 9. FIG. 12(b) shows a side view of the threaded end cap of FIG. 9 looking into the column receiving end thereof. The radial slots 720 are clearly shown therein as is the central aperture 710 and the O-ring groove 730.

A further feature of the invention is disclosed with respect to FIGS. 13(a) and (b). An adaptor for connecting a flanged column to a threaded column such as that illustrated in FIG. 8 of the present invention is depicted in FIGS. 13(a) and (b). The adaptor 800 includes a first flanged portion 810 and a second threaded portion 820. As seen with reference to FIG. 13(b), the first and second portions extend substantially transversely with respect to each other.

The flanged portion 810 includes a plurality of peripherally positioned, spaced apertures 812, by which the adaptor can be mounted to a flanged reservoir column. The threaded portion is provided with threads 822 designed to mate with the threads provided on the end portions of a threaded chromatography column. A space 824 is provided intermediate the flanged and threaded portions of the adaptor to receive an O-ring to seal the junction of the assembled columns.

The use of the above adaptor enables a flanged reservoir column to be used to pack a threaded chromatography column in an efficient manner.

Although the invention has been described herein with reference to particular means, materials and embodiments, it is understood that the invention is not to be limited to the particulars disclosed herein, and that the invention extends to all equivalents within the scope of the independent claims.

What is claimed is:

1. A slurry packing compressor for use in a chromatographic column adapted to contain a bed of particles comprising a slurry, said packing compressor comprising:
   a generally cylindrical metallic piston;
   means for receiving resilient means adapted to seal an interface of said chromatographic column and said piston;
   means for enabling material to be separated to be injected into said bed of particles;
   means for dispersing the material to be separated throughout the chromatography column, said dispersing means comprising a plurality of radially extending grooves provided in a slurry facing end surface of said generally cylindrical metallic piston; and
   means for retaining a frit comprising a threaded portion, said piston including a threaded portion adjacent the slurry contacting end face of said piston and adapted to engage said threaded portion of said frit retaining means, said frit retaining means further comprising means for receiving a frit sealing means.

2. The slurry packing compressor according to claim 1, said receiving means comprising a plurality of annular grooves provided in a cylindrical surface of said piston, each said groove adapted to receive resilient sealing means.

3. The slurry packing compressor according to claim 2, each said resilient sealing means comprising a resilient O-ring and a backup spacer member.

4. The slurry packing compressor of claim 3, wherein said backup spacer member comprises a split ring of glass loaded polymer.

5. The slurry packing compressor of claim 3, wherein said resilient O-ring is positioned within each said groove to be closer to a slurry bed facing end surface of said piston.

6. The slurry packing compressor of claim 3, said piston further comprising means for applying a hydraulic packing pressure against a slurry in said column.

7. The slurry packing compressor of claim 6, said piston further comprising means for maintaining a packed slurry bed during use of said column for separation.

8. The slurry packing compressor of claim 1, said frit means further comprising means for mating with a tool for tightening and loosening said frit retaining means with respect to said piston.

9. The slurry packing compressor according to claim 1, said frit retaining means further comprising means for receiving a slurry scraping member.

10. The slurry packing compressor according to claim 9, said slurry scraping means comprising an annular member threadably engageable with a mating threaded portion of said frit retaining means.

11. The slurry packing compressor of claim 1, said means for enabling comprising a bore extending through said piston.

12. The slurry packing compressor according to claim 11, said bore comprising means for sealably mating with a supply line for delivering material to be separated through said piston into a packed bed retained in said column.

* * * * *